United States Patent [19]

Mutzhas

[11] Patent Number: 4,558,700
[45] Date of Patent: Dec. 17, 1985

[54] UV RADIATION DEVICE FOR PHOTOTHERAPY OF DERMATOSES, ESPECIALLY PSORIASIS

[76] Inventor: Maximilian F. Mutzhas, Sonnenstr. 17, D-8000 Munchen 2, Fed. Rep. of Germany

[21] Appl. No.: 518,798
[22] PCT Filed: Dec. 23, 1982
[86] PCT No.: PCT/EP82/00273
 § 371 Date: Jul. 18, 1983
 § 102(e) Date: Jul. 18, 1983
[87] PCT Pub. No.: WO83/02233
 PCT Pub. Date: Jul. 7, 1983

[30] Foreign Application Priority Data
 Dec. 24, 1981 [DE] Fed. Rep. of Germany ....... 3151494

[51] Int. Cl.$^4$ ............................................. A61N 5/06
[52] U.S. Cl. ................... 128/395; 250/504 R
[58] Field of Search ..................... 128/303.1, 395–398; 313/621, 636; 250/504, 474.1, 372

[56] References Cited
U.S. PATENT DOCUMENTS

| | | | |
|---|---|---|---|
| 3,818,914 | 6/1974 | Bender | 128/396 |
| 3,986,513 | 10/1976 | Stuhl | 128/395 |
| 4,103,175 | 7/1978 | Levin | 250/504 |
| 4,155,025 | 5/1979 | Dobrusskin et al. | 313/621 |
| 4,177,384 | 12/1979 | Wolff | 250/504 |
| 4,246,905 | 1/1981 | Corth | 128/395 |
| 4,272,679 | 6/1981 | Blades | 250/372 |
| 4,279,254 | 7/1981 | Boschett et al. | 128/395 |
| 4,298,005 | 11/1981 | Mutzhas | 128/396 |
| 4,354,139 | 10/1982 | Konijnendijk et al. | 313/636 |
| 4,372,680 | 2/1983 | Adams et al. | 250/474.1 |

FOREIGN PATENT DOCUMENTS 813118 5/1959 United Kingdom .

Primary Examiner—Edward M. Coven
Assistant Examiner—Max F. Hindenburg
Attorney, Agent, or Firm—Learman & McCulloch

[57] ABSTRACT

The invention relates to a UV radiation device for phototherapy of dermatoses, especially psoriasis, which produces UV radiation the radiation intensity $E_2$ of which present in the effective area in the wavelength range below 300 nm is substantially less than the radiation intensity $E_1$ in the wavelength range between 300 and 310 nm, the radiation dose being between 0.7 and 1.0 times the erythema threshold dose. Such a UV radiation device is distinguished by good therapeutic effectiveness and the avoidance of undesirable side effects.

12 Claims, No Drawings

UV RADIATION DEVICE FOR PHOTOTHERAPY OF DERMATOSES, ESPECIALLY PSORIASIS

The invention relates to a UV radiation device for phototherapy of dermatoses, especially psoriasis.

BACKGROUND OF THE INVENTION

Approximately 2% of the population suffer from psoriasis, a flaking of the skin caused by a gene defect. A greatly increased rate of cell division (cell proliferation) in the basal layer of the epidermis gives rise to the flaky focus of the psoriasis which leads to severe physical and psychological effects.

The object of psoriasis therapy is to cause the focus to recede in order to make the skin free of flakes and keep it in this condition. At present therapy takes the form of treatment by chemotherapy, photochemotherapy and phototherapy.

In chemotherapy medication is orally administered or applied to the skin. In most cases this involves not only considerable side effects but also pain. There is also the disadvantage that chemotherapy can only be carried out on an in-patient basis in clinics.

Photochemotherapy uses medication in combination with UV radiation. In the Goeckermann therapy which has been used for a long time, tar is applied to the skin and then UV irradiation is carried out. In order for therapy to be successful, radiation must be applied until the skin shows an erythema (sunburn).

A modern type of photochemotherapy is known as PUVA. In this form of therapy a photosensitising medicament (Psoralen) is orally administered or applied to the skin. This is followed by irradiation with UV-A in the wave length range between 310 and 440 nm. The photosensitising medicament serves to make the skin more sensitive to the longwave UV-A radiation.

In this known method devices used as UV radiation sources either contain UV emitting fluorescent lamps (UV-A low pressure radiation devices) or mercury high pressure radiation devices, xenon radiation devices or mercury high pressure radiation devices doped with metal halides. The shortwave radiation below 315 nm is generally suppressed by filters in these devices.

In order for therapy to be successful, in this known method an erythema must also be produced, and this causes pain. In addition the skin—and, in the case of oral administration of Psoralen, also the eyes—cannot be exposed to daylight for several hours after administration of the medicament since otherwise considerable damage can occur. This means that the patients must either stay for several hours in the clinic or must be treated as in-patients. Depending upon the skin sensitivity the radiation times range from a few minutes to of the order of one hour.

On average this PUVA therapy requires 20 to 25 irradiation sessions, and in the course of the therapy a considerable browning of the skin (pigmentation) takes place. In the case of oral administration of Psoralen it is also of significance that a not inconsiderable number of patients show a poor toleration of this medicament.

In contrast to this photochemotherapeutic method, in phototherapy the therapeutic effects of UV radiation are used without the additional use of medication.

Earlier methods used mercury vapour high pressure radiation devices (home sunlight, high sunlight). Nowadays there are a number of different UV radiation sources with different spectral distribution. For psoriasis therapy UV fluorescent lamps are used which are known as UV-B lamps ("Sunlamp") and their emission spectrum in the UV range is from approximately 270 nm to approximately 365 nm. More than half of the UV energy is radiated in the range between 270 and 315 nm.

Some UV fluorescent lamps are also used in which the UV-B proportion (under 320 nm) is a very low percentage whilst the UV-A proportion (over 320 nm) is very high. These lamps are frequently known as UV-A lamps ("Blacklight"). Their emission spectrum in the UV range is from approximately 300 to 400 nm.

For the so-called SUP therapy (selective UV therapy) mercury vapour high pressure radiation devices doped with metal halide vapour are mostly used in which the emission spectrum in the UV range extends from approximately 250 nm to 400 nm. The wavelength range from approximately 290 to 335 nm is regarded as therapeutically effective.

In this phototherapeutic method radiation times which do not cause any erythema (sunburn) are used at first. However, in the course of the phototherapy the dose is increased so that erythema occurs. The minimal erythema is the slightest perceptible reddening of the skin; it is also known as the erythema threshold. The more intense an erythema is the more unpleasant are its side effects. These correspond to the side effects of sunburn or of burning (tightening, itching, pain and reddening, peeling, blistering, fever).

A further method of therapeutic treatment of psoriasis is known as SHIP (super high-intensive phototherapy). It makes use of the wavelength range from 320 to 330 nm. The proportion of the radiation lying below 320 nm is largely filtered out, but not the radiation above 330 nm. The radiation times are in the region of half an hour. On average approximately 30 radiation sessions are necessary before therapy is successful. In this method also a pigmentation of the skin occurs as a side effect.

SUMMARY OF THE INVENTION

It is the object of the present invention to provide a UV radiation device for phototherapy of dermatoses, especially psoriasis, which makes it possible to achieve effective healing with short radiation times and a limited number of radiation sessions without causing undersirable side effects.

The invention will be described using conventional terms such as radiation intensity, effective radiation area, radiation dose and erythema threshold dose. Radiation intensity is expressed as watts divided by the square of the distance (in meters) from the UV radiation device to the subject being irradiated. Effective radiation area is the area irradiated by the radiation device at the distance from the latter to the irradiated subject. Radiation dose is the sum of the radiation emitted or received per unit of time. Erythema threshold dose is the radiation required to produce perceptible reddening of the skin of the subject being irradiated.

The object of the invention is achieved in the UV radiation device according to the invention by the following features:

(a) The radiation device produces UV radiation the radiation intensity $E_2$ of which present in the effective area in the wavelength range below 300 nm is substantially less than the radiation intensity $E_1$ in the wavelength range between 300 and 310 nm, where $E_2$ is at most 0.35 $E_1$, if the radiation intensity below 295 nm is not greater than 0.01 $E_1$, in which $E_2$ is at most between 0.35 $E_1$ and 0.2 $E_1$, if the radiation intensity below a wavelength lying between 295 nm and 290 nm is not greater than 0.01 $E_1$, and in which in all other cases $E_2$ is at most 0.2 $E_1$;

(b) the radiation dose (time integral of the radiation intensity) is between 0.7 and 1.0 times the erythema threshold dose.

DETAILED DESCRIPTION

The invention is based upon the knowledge that for phototherapy of psoriasis UV radiation in the wavelength range between 300 and 310 nm is most favourable because it slows down the rate of cell division (cell proliferation) in the epidermis. The intentional use of this wavelength range between 300 and 310 nm distinguishes the UV radiation device according to the invention from the devices which are used in the above-mentioned SHIP method and operate in the range between 320 and 330 nm. The considerable technical and therapeutic advance achieved by the invention by contrast with the known devices is understandable when one considers that even in the wavelength range between 310 and 320 nm the so-called psoriasis threshold (i.e. the radiation dose at which psoriasis therapy is successful) requires a radiation dose which is higher by a tenth power than the radiation dose necessary in the wavelength range between 300 and 310 nm.

On the other hand, it is essential knowledge for the invention that the radiation intensity $E_2$ in the wavelength range below 300 nm must be less than the radiation intensity $E_1$, in the wavelength range between 300 and 310 nm. It would be desirable to suppress as far as possible any radiation in the wavelength range below 300 nm. However, in view of the desired high radiation intensity in the wavelength range between 300 and 310 nm this is not easily possible at an acceptable cost with the filters available at present (finite edge inclination of the filter). According to the invention the radiation intensity $E_2$ in the wavelength range below 300 nm is therefore limited so that in the therapeutic treatment the psoriasis threshold (i.e. the therapy threshold) is exceeded before the erythema threshold is reached. The limitation of the radiation intensity $E_2$ in the wavelength range below 300 nm is particularly important in this connection because in this wavelength range the erythema threshold is mostly higher than the psoriasis threshold.

If the radiation dose produced by the UV radiation device according to the invention (this should be understood as the time integral of the radiation intensity) is between 0.7 and 1.0 times the erythema threshold dose, then on the one hand this ensures the reliable triggering of a psoriasis therapy effect (taking account of individual deviations) but on the other hand prevents the erythema threshold from being exceeded.

In this way by using the UV radiation device according to the invention a pigmentation of the skin is also avoided in contrast to the known phototherapeutic method described above. In fact it has been shown that pigmentation occurring as a side effect of phototherapeutic treatment has distinct therapeutic disadvantages since the melanin which causes the pigmentation absorbs a large proportion of the penetrating UV radiation before it can be therapeutically effective in the basal layer. As a result when pigmentation occurs the radiation time must be lengthened. By contrast the UV radiation device according to the invention facilitates a substantial shortening of the radiation time or a reduction in the number of radiation sessions necessary.

The limitation according to the invention of the radiation intensity below 300 nm is also significant from the further point of view that this radiation (below 300 nm) in combination with radiation in the wavelengths between 300 and 310 nm can lead to a reversal of the therapeutic effect.

According to an advantageous embodiment of the radiation device according to the invention the radiation intensity $E_1$ present in the effective area in the wavelength range between 300 and 310 nm lies between 0.5 and 200 $Wm^{-2}$, preferably between 1 and 100 $Wm^{-2}$, preferably between 2 and 80 $Wm^{-2}$, preferably between 5 and 50 $Wm^{-2}$.

Radiation between 800 and 1400 nm is advantageously reduced, radiation above 1400 nm is advantageously completely suppressed. Both can be achieved by the use of a filter layer of water 5 to 15 mm, preferably approximately 10 mm, thick.

Radiation between 400 and 600 nm is advantageously largely suppressed—preferably by the use of a filter of blue violet or black glass.

The same applies to radiation between 330 and 440 nm, which is achieved by the use of a UV-permeable greenish yellow glass.

A UV radiation device according to the invention can use at least one metal halide vapour radiation device (without mercury) as the radiation source. It has the advantage that when switched on it immediately gives off the greater part of its power, and this is of significance above all in the case of short radiation times.

A further embodiment of the radiation device according to the invention uses at least one mercury vapour high pressure radiation device doped with metal halide vapour.

In both the types of radiation device referred to above halides of iron, nickel, cobalt, tin, zinc, indium, gallium, thallium, antimony and/or bismuth can be used individually or in combination as metal halides.

A further variant of the radiation device according to the invention which is distinguished by a particularly economical production uses at least one UV-B fluorescent lamp as a radiation source. Instead of elementary mercury if can contain an amalgam, preferably indium amalgam, and is distinguished by a particularly high radiation yield.

In order to suppress the radiation below 300 nm the radiation device conveniently contains an edge filter the mean transmission of which between 300 and 310 nm is at least equal to 2.8 times the mean transmission between 295 and 300 nm and at least equal to 5 times the mean transmission between 250 and 300 nm.

The edge filter can be made from organic material. The organic material can be acrylic glass (polymethylmethacrylate PMMA) in which organic absorbers are dissolved.

The organic material of the edge filter can also be polyvinyl chloride (PVC) or polyethylene terephthalate.

The edge filter can also be constructed as an inteference filter and arranged in a water layer.

If a UV-B fluorescent lamp is used, then the edge filter can be applied directly to the lamp as a foil or layer of varnish.

A further particularly advantageous embodiment of the radiation device according to the invention uses a UV-B fluorescent lamp the blub of which has a colourless soda-lime glass approximately 1 mm thick and uses cerium-activated strontium aluminate, lead-activated strontium aluminate, cerium-activated strontium fluoride and/or cerium-activated calcium fluoride as the fluorescent substance. By means of this combination of glass and fluorescent substance the radiation intensity below 300 nm is suppressed to the extent provided according to the invention so that a separate edge filter is unnecessary.

The following examples serve for further explanation of the invention:

EXAMPLE 1

Two metal halide vapour radiation devices filled with bismuth halide (without mercury) are used with a power of 1000 W per device.

The radiation flux (between 300 and 310 nm) amounts to approximately 40 W per radiation device.

An edge filter type WG 305 (4 mm) made by Schott-/Mainz is used, as well as a reflector made from anodised aluminium.

The radiation intensity $E_1$ (in the wavelength range between 300 and 310 nm) amounts to approximately 8 $Wm^{-2}$.

The radiation intensity $E_2$ (in the wavelength range below 300 nm) amounts to 0.12 $E_1$.

The psoriasis threshold time $t_{s,ps}$ is 75 s and the erythema threshold time $t_{s,er}$ is 90 s.

By contrast if the filter is left off (using the same radiation devices) this produces the following values for the radiation intensities and the threshold times:
$E_1 = 20$ $Wm^{-2}$
$E_2 = 0.5 \cdot E_1$
$t_{s,ps} = 20$ s
$t_{s,er} = 10$ s It is noted, as in the use of an unfiltered radiation through the comparatively high radiation intensity $E_2$ (in the wavelength range below 300 nm) that the erythema threshold is reached earlier than the psoriasis threshold.

EXAMPLE 2

Five metal halide vapour high pressure radiation devices are used with iron halide and mercury (power 3000 W per radiation device).

The radiation flux amounts (in the wavelength range between 300 and 310 nm) to approximately 80 W per radiation device. Tempax (3.4 mm) made by Schott-/Mainz is used as a filter. Like the edge filter WG 305 used in example 1, this filter is a colourless glass with a steep absorption limit in the UV range. The reflector again is made from anodised aluminium.

This results in the following values for the radiation intensity $E_1$ (in the wavelength range between 300 and 310 nm) and $E_2$ (in the wavelength range below 300 nm) and the following values for the psoriasis threshold time and the erythema threshold time:
$E_1 = 50$ $Wm^{-2}$
$E_2 = 0.14 \cdot E_1$
$t_{s,ps} = 8$ s
$t_{s,er} 32$ 10 s On the other hand, if the filter is omitted, the following values are obtained:
$E_1 = 100$ $Wm^{-2}$
$E_2 = 5 \cdot E_1$
$t_{s,ps} = 3$ s
$t_{s,er} = 0.5$ s

EXAMPLE 3

Ten UV-B fluorescent lamps are used with a power of 100 W per lamp. The radiation flux amounts to 2 W per lamp (in the range 300–310 nm).

Soft PVC with a thickness of 0.45 mm is used as a filter. The reflector is made from anodised aluminium.

This produces the following values:
$E_1 = 6$ $Wm^{-2}$
$E_2 = 0.12 \cdot E_1$
$t_{s,ps} = 100$ s
$t_{s,er} = 100$ s If the filter is left off the following values are obtained:
$E_1 = 11$ $Wm^{-2}$
$E_2 = 0.9 \cdot E_1$
$t_{s,ps} = 30$ s
$t_{s,er} = 20$ s

EXAMPLE 4

Two metal halide vapour radiation devices are used with bismuth halide filling (without mercury) and a power of 2000 W per radiation device. The radiation flux is approximately 80 W per radiation device.

The edge filters WG 305 (3 mm), GG 19 (1.5 mm) and UG 11 (3 mm) made by Schott/Mainz are used as well as a water filter layer of 10 mm. In this way the radiation above 310 nm is also substantially suppressed. Of the three said edge filters made by Schott WG 305 is a colourless glass with a steep absorption limit in the UV range, GG 19 is a greenish yellow glass with UV permeability and UG 11 is a UV-permeable black glass.

In this embodiment also the reflector is made from anodised aluminium.

The following values are obtained:
$E_1 = 4$ $Wm^{-2}$
$E_2 = 0.04 \cdot E_1$
$t_{s,ps} = 160$ s
$t_{s,er} = 200$ s

EXAMPLE 5

Ten UV-B fluorescent lamps (of 100 W) are used with a colourless soda-lime glass bulb approximately 1 mm thick and a fluorescent substance which is formed by cerium-activated strontium aluminate, lead-activated strontium fluoride and/or cerium-activated calcium fluoride.

This produces the following values:
$E_1 = 2.2$ $Wm^{-2}$
$E_2 = 0.19 \cdot E_1$
$t_{s,ps} = 210$ s
$t_{s,er} = 240$ s The preceding five examples relate to whole body radiation devices. If examples 1, 2 and 4 are constructed as part body radiation devices then because of the reduction in the effective area considerably higher radiation intensities can be achieved.

EXAMPLE 6

For part body radiation a metal halide vapour radiation device is used with iron iodide and mercury and a power of 3000 W, also a Tempax filter (3.4 mm)—as in example 2—and a UG 11 filter (3 mm)—as in example 4. Measurements were:
$t_{s,ps} = 11$ s
$t_{s,er} = 14$ s

EXAMPLE 7

For full body radiation five radiation devices are used as in example 6, but with a power of 4000 W (per device) and also the same filters as in example 6. Measurements are:

$t_{s,ps} = 33$ s
$t_{s,er} = 42$ s

EXAMPLE 8

For part body radiation the same radiation device as in example 6 is used. In addition to the two filters referred to there the filter GG 19—as in example 4—is also used. The values obtained:

$t_{s,ps} = 110$ s
$t_{s,er} = 140$ s

EXAMPLE 9

For full body radiation the same radiation devices as in example 7 are used. The filter GG 19—as in example 4—is used in addition to the two filters referred to in example 7. Measurements are:

$t_{s,ps} = 330$ s
$t_{s,er} = 420$ s

EXAMPLE 10

For full body radiation (using an aluminium reflector) two bismuth halide radiation devices (without mercury) of 1000 W are used, in addition to a Tempax filter (3.4 mm) and a UG 11 filter (3 mm).
This produces the following values:

$t_{s,ps} = 110$ s
$t_{s,er} = 135$ s

EXAMPLE 11

In a variant of example 10 five bismuth halide radiation devices (with mercury) of 3000 W are used, as well as a Tempax filter (3.4 mm). Measurements are:

$t_{s,ps} = 5$ s
$t_{s,er} = 8$ s

EXAMPLE 12

In a variant of example 11 five bismuth halide radiation devices (with mercury) of 3000 W are used, as well as a Tempax filter (3.4 mm) and a UG 11 filter (3 mm). Measurements are:

$t_{s,ps} = 8$ s
$t_{s,er} = 12$ s

EXAMPLE 13

In a variant of example 12 for whole body radiation five bismuth halide radiation devices (with mercury) of 3000 W are used, as well as filters Tempax (3.4 mm), UG 11 (3 mm) and GG 19 (1.5 mm). Measurements are:

$t_{s,ps} = 55$ s
$t_{s,er} = 100$ s

I claim:

1. Radiation apparatus adapted for use in the phototherapy of dermatoses, including psoriasis, and capable of generating a radiation dose between 0.7 and 1.0 times the erythema threshold dose, said apparatus comprising UV radiation means for producing UV radiation in a wavelength range from below 300 nm to 310 nm, the radiation between 300 nm and 310 nm having a radiation intensity $E_1$ in an effective radiation area and the radiation below 300 nm having a radiation intensity $E_2$ in said effective radiation area, said intensities having the following relationships in said area for the purpose of preventing the erythema threshold from preceeding the dermatose treatment threshold:
    (a) the intensity $E_2$ is at most 0.35 $E_1$ if the radiation intensity below 295 nm is not greater than 0.01 $E_1$;
    (b) the intensity $E_2$ is at most between 0.35 and 0.2 $E_1$ if the radiation intensity between 295 nm and 290 nm is not greater than 0.01 $E_1$; and
    (c) the intensity $E_2$ is in all other cases at most 0.2 $E_1$.

2. Apparatus according to claim 1 wherein the radiation intensity $E_1$ in said effective area in the wavelength range between 300 and 310 nm is between 0.5 and 200 $Wm^{-2}$.

3. Apparatus according to claim 1 wherein the radiation intensity $E_1$ in said effective area in the wavelength range between 300 and 310 nm is between 1.0 and 100 $Wm^{-2}$.

4. Apparatus according to claim 1 wherein the radiation intensity $E_1$ in said effective area in the wavelength range between 300 and 310 nm is between 2 and 80 $Wm^{-2}$.

5. Apparatus according to claim 1 wherein the radiation intensity $E_1$ in said effective area in the wavelength range between 300 and 310 nm is between 5 and 50 $Wm^{-2}$.

6. Apparatus according to claim 1 including filter means for suppressing UV radiation in excess of 330 nm.

7. Apparatus according to claim 6 wherein said filter means comprises UV permeable greenish yellow glass.

8. Apparatus according to claim 7 wherein said filter means comprises blue violet or black glass.

9. Apparatus according to claim 1 wherein said radiation device includes a radiation source composed of metal halide vapour without mercury.

10. Apparatus according to claim 1 wherein said radiation device includes a radiation source composed of mercury vapour doped with metal halide vapour.

11. Apparatus according to claim 10 wherein said metal halide is selected from the class consisting essentially of iron, nickle, cobalt, tin, zinc, indium, gallium, thallium, antimony, and bismuth and combinations thereof.

12. Apparatus according to claim 1 including edge filter means the mean transmission of which between 300 and 310 nm is at least equal to 2.8 times its mean transmission between 295 and 300 nm and at least 5 times its mean transmission between 250 and 300 nm.

* * * * *

UNITED STATES PATENT AND TRADEMARK OFFICE
CERTIFICATE OF CORRECTION

PATENT NO. : 4,558,700
DATED : December 17, 1985
INVENTOR(S) : Maximilian F. Mutzhas It is certified that error appears in the above-identified patent and that said Letters Patent are hereby corrected as shown below:

Column 4, line 68, change "blub" to -- bulb --.

Column 5, line 62, change "$t_S,er32\ 10\ s$" to --$t_S,er=10\ s$--.

Signed and Sealed this

Seventeenth Day of June 1986

[SEAL]

Attest:

DONALD J. QUIGG

Attesting Officer

Commissioner of Patents and Trademarks